United States Patent
Tuchscherer et al.

(10) Patent No.: US 9,057,095 B1
(45) Date of Patent: Jun. 16, 2015

(54) METHOD AND KIT FOR TESTING CARBAMATES IN AMINE-CURED EPOXY MATERIALS

(75) Inventors: Melissa Tuchscherer, Kansas City, MO (US); Perry Kilpatrick, Kansas City, MO (US); Richard Slawecki, Warminster, PA (US); Fernando Manuel Rubio, Doylestown, PA (US)

(73) Assignee: Abraxis LLC, Warminster, PA (US)

( * ) Notice: Subject to any disclaimer, the term of this patent is extended or adjusted under 35 U.S.C. 154(b) by 320 days.

(21) Appl. No.: 13/350,405

(22) Filed: Jan. 13, 2012

Related U.S. Application Data

(60) Provisional application No. 61/433,207, filed on Jan. 15, 2011.

(51) Int. Cl.
| | |
|---|---|
| *C12Q 1/46* | (2006.01) |
| *C12Q 1/34* | (2006.01) |
| *G01N 31/22* | (2006.01) |
| *G01N 33/573* | (2006.01) |

(52) U.S. Cl.
CPC *C12Q 1/46* (2013.01); *G01N 31/22* (2013.01); *C12Q 2334/00* (2013.01)

(58) Field of Classification Search
None
See application file for complete search history.

(56) References Cited

PUBLICATIONS

Croll "Atmospheric gases and the hardening of an amine-cured epoxy coating" Journal of Coatings Technology 1980 (51)664 65-69.*
Galgani et al "In Vitro inhibition of acetylcholinesterase from four marine species by organophosphates and carbamates" (Bull. Environ. Contam. Toxicol. 1990 45: 243-249).*
Odegaard et al (Old Poisons, New Problems 2005 Alt Mira Press p. 61).*
Elctometer (Datasheet Jan. 10, 2004).*
Abraxis, Package Insert for OP/Carbamate Kit (marked R1111410: on second page, second column) (Dec. 2010 or earlier).
Burton, B., Amine-Blushing Problems? No Sweat! Presented at the Fall 2001 Epoxy Resin Formulators' Meeting of the Society of the Plastics Industry, Huntsman Corporation, (2001).
Chitlaru, T., et al., Modulation of Circulatory Residence of Recombinant Acetylcholinesterase Through Biochemical or Genetic Manipulation of Sialylation Levels. Biochem. J., (1998), 336, 647-658.
Ellman, G,L. et al., A New and Rapid Colorimetric Determination of Acetylcholinesterase Activity. Biochemical Pharmacology, (Jul. 1961), vol. 7, Issue 2, (Abstract Only).
Kikuchi, T., et al., Piperidine-4 methanthiol Ester Derivatives for a Selective Acetylcholinesterase Assay. Biol. Pharm. Bull, (2010), 33(4), 702-706.
Komers, K., et al., Kinetics and Mechanism of Hydrolysis of Acetylthiocholine by Butyrylcholine Esterase. Z. Naturforsch., (2002), 57c, 1072-1077.
Main, A.R., et al., A Subunit-Sized Butyrylcholinesterase Present in High Concentrations in Pooled Rabbit Serum. Biochem. J. (1977) 167, 367-376.
Schopfer, L.M., et al., Mutants of Human Butyrylcholinesterase With Organophosphate Hydrolase Activity; Evidence That HIS117 is a General Base Catalyst for Hydrolysis of Echothiophate. J Med Chem Def, (Aug. 2004), vol. 2.
Sturm, A., et al., Different Sensitivity to Organophosphates of Acetylcholinesterase From Three-Spined Stickleback (*Gasterosteus aculeatus*): Application in Biomonitoring. Environmental Toxicology, (2000),vol. 19, Issue 6, (Abstract Only).
Valdes-Ramirez, G. et al., Acetylcholinesterase-Based Biosensors for Quantification of Carbofuran, Carbaryl, Methylparaoxon, and Dichlorvos in 5% Acetontrile. Anal Bioanal Chem, (Oct. 2008), 392(4), (Abstract Only).
Valdes-Ramirez, G., et al., Automated Resolution of Dichlorvos and Methylparaoxon Pesticide Mixtures Employing a Flow Injection System With an Inhibition Electronic Tongue. Biosens Bioelectron, (Jan. 2009),1;24(5), (Abstract Only).
Velan, B., et al., Recombinant Human Acetylcholinesterase Secreted from Transiently Transfected 293 Cells as a Soluble Globular Enzyme. Cellular and Molecular Neurobiology, (1991), vol. 11, No. 1, 143-156.

* cited by examiner

Primary Examiner — Suzanne M Noakes
Assistant Examiner — Gerard Lacourciere
(74) Attorney, Agent, or Firm — Allan H. Fried

(57) ABSTRACT

The present invention provides a kit and a method of testing for carbamates in amine cured epoxies. The method and kit are based on the use of an enzyme that is inhibited by carbamates. A specific embodiment of the kit includes acetylthiocholine (ATC), dithio-bis (2-nitrobenzoic acid) (DTNB), and acetyl-cholinesterase (ACh-E). In the corresponding method embodiment, the method comprises the steps of collecting carbamates from the epoxy, adding the collected carbamates to a solution, adding acetyl-cholinesterase (ACh-E) to the solution, adding acetylthiocholine (ATC) to the solution, adding dithio-bis (2-nitrobenzoic acid) (DTNB) to the solution, and ultimately measuring the intensity of the yellow color of the solution.

23 Claims, No Drawings

METHOD AND KIT FOR TESTING CARBAMATES IN AMINE-CURED EPOXY MATERIALS

CROSS REFERENCE TO RELATED APPLICATIONS

This application claims the benefit of U.S. Provisional Application No. 61/433,207 filed Jan. 15, 2011, which application is incorporated by reference in its entirety herein.

FIELD OF THE INVENTION

This invention relates to a method and a kit for testing for the presence of carbamates in amine cured epoxy materials.

BACKGROUND OF THE INVENTION

Amine cured epoxies are widely used. Amines and amine functional amides are common curing agents for high performance epoxy coatings. Epoxy resins which are cured, hardened, or crosslinked with multifunctional amines, i.e., amine compounds having three or more active amine hydrogens, are well known in the industry. These materials are widely used in applications such as coatings, adhesives, composites, and civil engineering applications such as formulations for flooring, In coating applications, amine cured epoxy formulations generally can be cured at room temperature to yield films with high mechanical strength, good water, chemical, and corrosion resistance, and excellent adhesion properties. Thus, they are often employed as primers and topcoats for large structures such as ships, bridges, and industrial plants and equipment, Many amine cured epoxy coatings if polymerized or cured using non-prescribed conditions such as cool ambient temperature or high humidity can develop problems referred to in the industry as amine blush . With primary amines, the amine that has migrated to the surface can react with $CO_2$ present in the air, ultimately resulting in the formation of carbamates on the surface of the epoxy coating. The presence of carbamates can lead to intercoat adhesion failures if the film is re-coated. This is a serious problem because many epoxy coatings are over coated. The additional coatings are not limited to epoxy-based systems and can include other chemical coating systems (e.g., polyurethanes) in order to provide particular end-use properties, such as corrosion resistance, weatherability, etc.

When determining if an epoxy coating can be over coated, it is important to determine if the coating exhibits the phenomenon of amine blush. Similarly when analyzing why an epoxy coating could not be successfully overcoated, it is important to determine whether the cause was amine blush. When blush is visible to the naked eye, it can appear as a thin spotty or greasy layer ranging in color from white to amber. Previous quick field tests relied on pH to determine the presence of amine blush as a result of the presence of carbamates; however in many cases the raised pH was not caused by the presence of carbamates. The present invention identifies that carbamates are present and does not rely on raised pH for that purpose. It can be done as field test—at the location where the epoxy surface was created—or in the laboratory.

BRIEF SUMMARY OF THE INVENTION

In its most general aspect, the invention is a method for identifying the presence of carbamates in amine-cured epoxies. A related aspect of the invention is a kit for carrying out that method. The method is based on the fact that carbamates inhibit the catalytic action of certain enzymes, such as certain cholinesterases, including acetyl-cholinesterase. This reduced catalytic ability can be detected by using an assay in which the activity of the enzyme results in an aqueous solution that has a distinctive color. The usefulness of the invention is that it can be used to determine whether carbamates (amine blush) are present in an amine-cured epoxy material.

DETAILED DESCRIPTION OF THE INVENTION

In the particular embodiment of the invention described in detail in the present application, the invention takes advantage of the following enzymatic and chemical reactions: Acetyl-cholinesterase (ACh-E) will, in the absence of an inhibitor, react with acetylthiocholine (ATC) such that one of the products has a thiol group. The thiol group will, in aqueous solution, react with 5,5'-dithiobis-2-nitrobenzoic acid (DTNB), generating a compound that imparts a yellow color to the solution. Carbamates inhibit the action of ACh-E and therefore their presence will result in a reducing amount of yellow color.

The color assay is a modification of the original Ellman spectrophotometrical method for cholinesterase activity determination, it uses 5,5'-dithiobis-2-nitrobenzoic acid (DTNB, Ellman's reagent) as a chromogen and records the level of cholinesterase activity as an increase of absorbance at 412 nm. DTNB is a chemical used to quantify the concentration of thiol groups in a sample. Thiols react with this compound, cleaving the disulfide bond of DTNB to give 2-nitro-5-thiobenzoate ($NTB^-$), which ionizes to the $NTB^{2-}$ dianion in water at neutral and alkaline pH. This $NTB^{2-}$ ion has a yellow color.

The use of the plural "carbamates" in this provisional patent application takes into account that the number of carbamate molecules active in the method of this invention will be very large—even if they are all of identical chemical structure.

Method of the Invention

In a general aspect, the present invention is a method for confirming the presence of, or detecting, carbamates in an amine-cured epoxy material, said method comprising the steps of:
a. Collecting, in an aqueous solution (a solution comprising water), carbamates from said material, said aqueous solution being a test sample;
b. adding an enzyme whose activity is inhibited by carbamates (e.g. acetyl-cholinesterase (ACh-E), also referred to as an "acetylcholinesterase") to the test sample;
c. adding a substrate for said enzyme (e.g., acetylthiocholine (ATC) when the enzyme is acetyl cholinesterase) to the test sample, such that the cleavage of the substrate by the enzyme will result in either a modified substrate or a substrate cleavage product;
d. adding a chromogen (such as 5,5'-dithiobis-2-nitrobenzoic acid (DTNB) when the enzyme is ACh-E and the substrate is ATC) to the test sample, such that said chromogen reacts with either the modified substrate or the substrate cleavage product so as to alter or intensify the color of the test sample; and
e. subsequent to the foregoing steps (a), (b), (c), and (d), determining the intensity of the color of the test sample (such as a yellow color when ACh-E , ATC and DTNB are used).

In a related aspect, the enzyme is a cholinesterase, the substrate added is such that the cleavage of the substrate results in a cleavage product that comprises a thiol group, and the chromogen reacts with the cleavage product so alter the color of the test sample.

In a specific related aspect, the smaller the intensity of the color of the test sample, the higher the probability that carbamates are present in the test sample.

The method and its possible variations are summarized in more detail at various places in this patent application.

In the Claims at the end of the specification of this application, in the section starting "What is claimed", various Claims are introduced by the phrase "The method of claim 1 wherein . . . ". These dependent claims include claim limitations that could be applied to all other dependent claims to methods. As a result, applicant may amend those dependent claims to also be dependent on Claims other than claim 1.

Similarly, in the Claims at the end of the specification of this application, in the section starting "What is claimed", various Claims are introduced by the phrase "The kit of claim 9 wherein . . . ". These dependent claims include claim limitations that could be applied to all other dependent claims to kits. As a result, applicant may amend those dependent claims to also be dependent on Claims other than claim 9.

Cholinesterases and their Substrates

The acetyl-cholinesterase used in the method can either be a naturally occurring or a recombinant acetyl-cholinesterase. In a particular aspect of the invention, the acetyl-cholinesterase is a recombinant acetyl-cholinesterase. Recombinant acetyl-cholinesterase can be derived from eukaryotic (preferred) or prokaryotic cells in which the amino acid sequence of the ACh-E differs from that of naturally occuring ACh-E because the DNA coding for the ACh-E has been altered by human intervention.

ATC is an appropriate substrate for ACh-E in the methods of the present invention, as are other thiocholines provided they can be similarly hydrolyzed by ACh-E to generate a product with a thiol group. Similarly, salts of ATC and other thiocholines are appropriate substrates for ACh-E provided they can be similarly hydrolyzed by ACh-E to generate a product with a thiol group.

A preferred recombinant cholinesterase is ID# B-394 available from GTP Technology, Immeuble Biostep, Rue Pierre et Marie Curie—BP 48184, 31681 Labége Cedex, France.

A possible source of a naturally occuring acetyl cholinesterase is Sigma-Aldrich.

Other cholinesterases may also be used in the method, Examples of such cholinesterases are butyryl cholinesterase (see, for example, L. M. Schopfer et al.; J Med Chem Def, vol. 2, Aug. 2004) and electric eel acetyl cholinesterase.

Butyrylthiocholine (BTC) is an appropriate substrate for butyryl cholinesterase in the methods of the present invention as are other thiocholines provided they can be similarly hydrolyzed by butyryl cholinesterase to generate a product with a thiol group. Similarly, salts of BTC and other thiocholines are appropriate substrates for butyryl cholinesterase provided they can be similarly hydrolyzed by butyryl cholinesterase to generate a product with a thiol group.

Epoxy Resins, Amine Curing Agents, and Carbamates

There are numerous epoxy resins that are subjected to amine curing. This invention is intended to be applicable to all amine-cured epoxy materials. Similarly, there are numerous amines that can be used as curing agents. The amine can be a primary, secondary or tertiary amine. Examples of amines commonly used for curing epoxies include, but are not limited to, isophorone diamine, cyclohexylamine, bis(p-aminocyclohexylmethane), and aliphatic amines.

Amines that are low-molecular weight primary amines (e.g., aliphatic amines and cyclo-aliphatic amines) are particularly prone to forming carbamates as a result of the curing process.

Carbamates that form as a result of amine-curing of epoxies are normally ammonium carbamates or substituted ammonium carbamates.

"Swab Sampling Technique" for Creating a Test Sample

The swab samping technique utilizes a Q-tips (or other swabbing device,such as a "towlette") premoistened with a solvent that will extract the carbamates from the cured epoxy material. For example, 70% isopropy alcohol (IPA) can be used to swab an area (e.g., one inch by one inch) of epoxy material suspected of having amine blush. The swab is placed in a test tube containing a solvent (for example, 1 milliliter) in which cholinesterase will be active and carbamates will be soluble. Examples of such solvents are Assay Buffer or water. The content of that tube is designated herein as a "Test Sample."

Immersion Sampling Technique for Creating a Test Sample

In the immersion sampling technique (also referred to as the "Chip Method"), one or more fragments (e.g., chips or shavings) from the epoxy material area to be tested are placed in a test tube containing, for example, 1 ml of Assay Buffer or water. The content of that tube is designated herein as a "Test Sample". If the sample fragments are small chips or shavings, a small chip approximately ⅛ inch to ¼ inch wide by ½ inch long, or enough shavings to approximate that size, is placed in the test tube.

In the Chip Method, in some instances, more efficient detection of blush is achieved if the buffer in which the chips or shavings are immersed also contains an alcohol, such as methanol or isopropyl alcohol. Examples of the final concentrations of the alcohol that may prove useful include, but may not be limited to, those in the range 5 to 24 percent on a volume basis.

Positive Controls

A positive control is analyzed to make sure that the method of the invention, or a kit of the invention, is capable of detecting the presence of carbamates should they be present. The positive control is a solution of a carbamate at a known concentration—the source of the carbamates is a preparation of carbamates (preferably a highly purified preparation) rather than an amine-cured epoxy material. Preferred carbamates for use in the positive control are: Carbaryl, aldicarb, carbofuran; preferred concentrations are in the range 1 to 1,000 ppb. The concentration will be one that the conductor of the test expects to cause a decrease (preferably a decrease of at least a 20 percent) in the spectrophotometrically determined yellow color generated by the method or kit of the invention. Such a decrease is expected to be sufficient to result in a visually detectable decrease in the yellow color. If the positive control does not achieve the desired result (for example, a 20% reduction or a visually detectable decrease), it is an indication that the assay is not performing optimally.

The positive control is subjected to the same method as the epoxy material being tested for the presence of carbamates. If the material is being swabbed or dipped with a Q tip that was immersed in 70% IPA), then the positive control will have, in the Assay Buffer or water, a Q-tip that was immersed in 70% IPA (but did not swab an epoxy material). The positive control tube will, as noted above, have enough carbamate to result in a reduced intensity of yellow color (For example between 1 and 1000 nanograms of carbamates per ml of Assay Buffer).

If the material being tested consists of chips or shavings immersed in a solution (e.g., assay buffer or water), the positive control will consist of that solution without any chips or shavings—but will contain enough carbamates to result in a reduced intensity of yellow color.

If the material being tested contains a substance that, even in the absence of carbamates will inhibit cholinesterases (either directly or by altering the pH of the assay), it will be necessary to determine how much decreased color is attributed to that substance and how much is attributable to carbamates.

Negative Control

A negative control is analyzed to make sure that, in the absence of carbamate, the method or kit will indicate that, indeed, no carbamate is present. The negative control can be an aqueous solution of the same composition as that in which a Q-tip or epoxy fragments are immersed.

The negative control is subjected to the same method as for the material being tested for the presence of carbamate—except that the swabbing device, if present, has not swabbed an epoxy surface and no epoxy fragment is present. If the material is being swabbed with a Q tip that was immersed in 70% IPA, then the negative control will have a Q-tip that was immersed in 70% IPA—but no wiping of the surface.

If the material being tested consists of chips or shavings immersed in a solution (e.g., Assay Buffer or water), the negative control can consist of that solution without any chips or shavings—and without any carbamates.

In the presence of excessive amine, such as amine from the material being tested, however, the test sample can develop a more intense yellow color than is developed by the negative control sample, and that needs to be taken into account in interpreting the results of the method. Should the test sample have a yellow color more intense than of the negative control sample, it cannot be ruled out that the test sample comprises a mixture of amines and carbamates and that the color increase caused by the amines is masking the color decrease that would otherwise have been caused by the carbamates in the absence of those amines, In general, if the test sample has a yellow color more intense than the negative control, additional analysis is needed to determine whether the additional color is due to excess amines or another cause.

The sample size is critical to ensure that the pH is preferably not outside of the range of the buffer solution, If there is a belief that high pH could be contributing to the yellow color, then a smaller sample size should be tested.

Preferred Implementation of the Method Using the Preferred Set of Reagents and Materials The reagents (or kit if a kit is used to implement the method) are allowed to reach ambient temperature (either room temperature or, if the method is performed outdoors, the ambient outdoor temperature) prior to performing the assay. The assay is preferably performed at a temperature in the range 65 to 80 ° F.

The following is a preferred implementation of the method:
1) Place a Q-tip swab (premoistened in 70% IPA) or chips or shavings in a test tube containing 1 milliliter of Assay Buffer or water (The"Sample Tube"; the sample is referred to as a "Test Sample"; if using Assay Buffer, the Assay Buffer consists of PBS (1.15 g/L of Sodium Phosphate Dibasic, 0.2 g/L Potassium Chloride, 8 g/L Sodium Chloride, 0.2 g/L Potassium Phosphate Monobasic, pH 7.4).
2) Add 3drops (0.12 milliliters, total) of ACh-E solution to the Sample Tube containing the swab or chips or shavings in Assay Buffer . The Ach-E Solution will consist of ACh-E at a concentration of 0.22 Units/ml in ACh-E Reconstitution Buffer, which Reconstitution Buffer is water with 0.1% Proclin). The ACh-E Solution will be made by adding Reconstitution Buffer to lyophilized ACh-E.
3) Cap the Sample Tube and shake it to mix the contents.
4) Allow the Sample Tube to stand for 30 minutes preferably at room temperature (65-80° F.); The reaction will, however, generally work in the range 45-110° F., with less color developed at the lower end of the range and more color at the higher end of the range,
5) Add 3 drops (0.12 milliliters, total) of ATC solution to the Sample Tube (The ATC Solution will consist of ATC at a concentration of 2.9 milligrams/ml in distilled water). The ATC Solution will be made by adding distilled water to lyophilized ATC.
6) Cap the Sample Tube and shake it to mix the contents.
7) Add 2 drops (0.08 milliliters, total) of DTNB to the SampleTube.
8) Cap the Sample Tube and shake it to mix the contents.
9) Allow the Sample Tube to stand for 30 minutes at room temperature.
10) Determine the amount of yellow color, either visually or spectrophotometrically by measuring absorbance at a wavelength in the range 405 (preferred) to 450 nanometers.

The negative and/or positive controls are preferably tested in parallel with the Test Sample (the material being tested for the presence of carbamates) but if that is not possible, as might be the case with a large number of Test Samples, then the negative and/or positive controls samples are preferably tested immediately before or after the Test Samples are tested. (Or, if desired, controls can be measured both before and after the Test Samples are tested.)

Based on the criteria described elsewhere in this provisional patent application, the data obtained with a Test Sample and the negative control (if any) and the positive control (if any) is used to determine whether there were carbamates in the Test Sample. Relating the carbamate concentration in the Test Sample to the carbamate concentration in the amine-cured epoxy material, or at or near its surface, is difficult unless there is reason to believe that all the carbamate has been extracted, for example from chips or shavings. However, the accumulation of data from applying the method of this invention to various amine-cured epoxy materials, including those made ostensibly from the same type of epoxy resins and the same curing method, can in any case be correlated with the chemical physical properties of the amine-cured epoxies tested (e.g. their inter coat adhesion properties) so that the carbamate concentration observed in the Test Sample becomes a useful predictor of whether a material has a level of carbamates that is too high and needs to be corrected by revision of the curing process.

Kits of the Invention

In a general aspect, a kit of the present invention will comprise the essential components of the method of the invention: an enzyme inhibitable by carbamates, a substrate for the enzyme, and a chromogen that reacts with either (i) the substrate as altered by the enzyme or (ii) with a substrate fragment resulting from substrate cleavage by the enzyme so that in either case (i) or (ii) the color of the chromogen in solution is altered. In a particular embodiment, the kit is one for confirming or demonstrating the presence of carbamates in an amine-cured epoxy material, said kit comprising acetylthiocholine (ATC), 5,5'-dithiobis-2-nitrobenzoic acid (DTNB), and acetyl-cholinesterase (ACh-E).

In a related aspect, the enzyme is a cholinesterase, the substrate is such that the cleavage of the substrate results in a cleavage product that comprises a thiol group, and the chromogen is one that reacts with the cleavage product in solution so as to change the color of the solution.

The kit will preferably contain a tube for a positive control sample and/or a tube for a negative control sample.

The kit will preferably further comprise a measuring device for measuring, or assisting in the measurement of, the size or amount of the epoxy material (e.g., a chip or a shaving) to be tested for the presence of carbamates. The measuring device will preferably provide a two-dimensional area to allow the kit user to prepare a fragment or collection of fragments that falls within dimensions which will not overcome the buffer solution or be below the detection limit for the carbamate. The top surface area is the important measurement as the phenomenon is mostly a surface phenomenon resulting from amine on the surface reacting with $CO_2$ and moisture in the atmosphere. Therefore a two-dimensional area can be provided by a template marked on it or into it impressed onto a two-dimensional flat surface to form a small impression, such that the perimeter of the template is chosen as one within which all epoxy fragments should fit if placed together on the template. The volume can be provided by a container whose internal volume (or a marked segment of the internal volume) is a preferred upper limit to the total volume of fragments to be tested in a sample. Preferred cross-sectional shapes to the volume are a circle, a square, and a rectangle. The preferred size of the area within the template perimeter is that equal to a rectangle approximately ⅛ inch to ¼ inch wide by ½ inch long. Other preferred shapes for the area could be a circle or square.

The kits of the present invention and their possible variations are summarized in more detail at various places in this provisional patent application.

In the kit, the ATC and Ach-E may or not be in aqueous solution (i.e., an appropriate diluent). They may be present, in separate containers, in lyophilized form. The kit will in that case preferably contain an appropriate aqueous solution(s) that can be added to the lyophilized ATC and ACh-E just before their use in the method.

Instructions in the Kit

It is desirable that the kits of the present invention be identified as having the aforementioned utility: The ability to detect carbamates in amine-cured epoxy materials. This identification can be carried out by a label or printed instructions, in or on the kit. The kit preferably comprises instructions on how to use the kit for detecting carbamates on amine-cured epoxy materials.

Storage of the Kit and Components

All reagents should be stored at preferably 2-8° C. The reagents can be stored at room temperature but the shelf life of the kit will be less than if it were stored at 2-8° C.

Kits

A kit is considered to be a collection of components, such as those specified for a kit herein, where the components are either: (1) in a box (or other container); or (2) in a set of boxes identified as being intended for use with contents of other boxes in the set. In the latter case, the fact that the contents of the various boxes can be used with each other for the use of analyzing amine blush and/or demonstrating the presence of carbamates can be in a box, on a box, in a document sent with a box, or in a document identifying the boxes and their intended use—such as would be in a printed catalogue or brochure inviting the reader to purchase the kit or an on-line advertisement inviting the reader to purchase the kit.

Precautions When Performing the Method

Appropriate measures to avoid contact of reagents with skin and mucous membranes should be taken. As with all assays, a consistent technique is the key to optimal performance. To obtain the greatest precision, each tube is treated in an identical manner. The analyst avoids drops touching the side of assay tube, When performing assay outdoors, one avoids direct sunlight during testing by keeping the test tubes in a container.

Further Preferred Aspects of the Kits of the Present Invention

The ACh-E is preferably in lyophilized form in a dropper bottle with a removable dropper cap.

The ATC is preferably in lyophilized form in a dropper bottle with a removable dropper cap.

The DTNB is preferably in a dropper bottle with a removable dropper cap.

One or more pipets are preferably part of the kit, for operations such as adding ACh-E Reconstitution Buffer to the lyophilized ACh-E or adding ATC Reconstitution Buffer to the lyophilized ATC, or Assay Buffer or water to the Sample Tube.

Test tubes with removable caps are useful for use as Sample Tubes.

In a particular embodiment, the kit will comprise a swabbing device. Examples of swabbing devices include, but are not limited to, a Q-tip and a towlette. The swabbing device is, optionally, pre-moistened.

If the swabbing device is premoistened, it is preferably in a sealed container that can be opened when the device is needed.

The kit may also contain components used to measure pH. Examples include, but are not limited to Hydrion pH paper or other paper whose color depends on the pH of the solution in which the paper is immersed.

EXAMPLES

Example 1

Nine amine-cured epoxy panels were tested. Also a positive control was tested. The panels were prepared by spraying them all with the same preparation, a preparation containing bisphenol A epoxy and amines. The panels were lined up and sprayed one after the other in a continuous spraying operation starting at one end of the line of panels and ending at the other end of the line.

The testing method was as follows, the results being summarized in Table 1:

1) A Q-tip swab (premoistened in 70% IPA) was used to swab a one inch by one inch area of the epoxy material and the Q-tip was placed in a test tube (a "Sample Tube") containing 1 milliliter of either Assay Buffer (samples denoted by"(B) in Table 1) or water (samples denoted by"(W) in Table 1) (if using the Assay Buffer, that Buffer consisted of PBS at pH 7.4). The tube contents are a "Test Sample". Table 1 shows whether the Q-tip was placed in a test tube containing Assay Buffer or a test tube containing water. For some epoxy panels, two Q-tips were used, each for a different area of the epoxy panel, one Q-tip placed in a test tube containing Assay Buffer the other in a test tube containing water,
2) Three drops (0.12 milliliters, total) of ACh-E solution was added to each Sample Tube containing the swab in Assay Buffer or water (The ACh-E solution consisted of a recombinant ACh-E, ID# B-394 available from GTP Technology. The ACh-E was at a concentration of 0.22 Units/ml in ACh-E Reconstitution Buffer, which Reconstitution Buffer is distilled water with 0.1% Proclin. According to the information provided by GTP Technology, one Unit will produce 1 μmol 5-thio-2-nitro-benzoic acid per minute at pH 7.0 at 25° C. when the enzymatic activity is evaluated by colorimetric assay described by Ellman et al. Biochem Pharmacol. Jul. 1961; 7:88-95).
3) Each Sample Tube was capped and shaken to mix the contents.
4) Each Sample Tube was allowed to stand for 30 minutes at room temperature (65-80° F.).
5) Three drops (0.12 milliliters, total) of ATC solution were added to each Sample Tube (The ATC was at a concentration of 2.9 milligrams/ml in distilled water).
6) Each Sample Tube was capped and shaken to mix its contents.
7) Two drops (0.08 milliliters, total) of DTNB were added to each Sample Tube;
8) Each Sample Tube was capped and shaken it to mix the contents.
9) Each Sample Tube was allowed to stand for 30 minutes at room temperature.
10) The intensity of each test sample was measured at 450 nm spectrophotometrically. Each was also compared visually to a negative control—an epoxy sample known to not exhibit blush—and assessed as indicating the presence ("pos") or absence ("neg") of carbamates. The results are shown in Table 1 below.

TABLE 1

| | Absorbance 450 Negative Control | Absorbance 450 Sample | Inhibition (%) | Interpretation |
|---|---|---|---|---|
| Panel 1 (B) | 2.484 | 0.985 | 61 | pos |
| Panel 2 (W) | 0.629 | 0.223 | 65 | pos |
| Panel 3 (B) | 1.706 | 0.645 | 62 | pos |
| Panel 4 (B) | 1.754 | 0.609 | 65 | pos |
| Panel 4 (W) | 0.624 | 0.322 | 49 | pos |
| Panel 5 (B) | 1.754 | 0.724 | 59 | pos |
| Panel 5 (W) | 0.624 | 0.266 | 58 | pos |
| Panel 6 (B) | 1.754 | 0.778 | 56 | pos |
| Panel 6 (W) | 0.624 | 0.457 | 27 | pos |
| Panel 7 (B) | 1.58 | 0.544 | 66 | pos |
| Panel 7 (W) | 0.394 | 0.111 | 72 | pos |
| Panel 8 (B) | 1.58 | 0.676 | 57 | pos |
| Panel 8 (W) | 0.394 | 0.109 | 73 | pos |
| Panel 9 (B) | 1.58 | 0.584 | 63 | pos |
| Panel 9 (W) | 0.394 | 0.086 | 78 | pos |

B = Buffer

TABLE 1-continued

| | Absorbance 450 Negative Control | Absorbance 450 Sample | Inhibition (%) | Interpretation |
|---|---|---|---|---|

W = Water

The data in Table 1 show that the color intensities were higher when the Q tip was immersed in Assay Buffer instead of water. Regardless of whether Assay Buffer or water was used, however, carbamates were detected in the panels tested.

The results show that when a Q-tip was immersed in Buffer, the color developed in the assay was more intense than when it was dipped in water. Also the negative control had a more intense color when Buffer rather than water was used.

The results also show some panel-to-panel variation in carbamate concentration, indicating that if a sprayed surface is tested for carbamates, more than one area of the surface should be tested.

Example 2

The testing method was also performed using Electric Eel ACh-E (EE ACh-E) as an enzyme and ATC-Chloride (ATC-C) as a substrate, (EEl ACh-E and ATC-C were obtained from Sigma.). The steps are briefly summarized here and the results are summarized in Table 2. It can be seen that the procedure was the same as in Example 1 except that the Chip Method was also tested and different enzymes and substrates were used (as well as some differences in their stock solution formulations).

The amine-cured epoxy test panel, in which blush had been induced, used for the Swab method was different from the amine-cured epoxy test panel, in which blush had been induced, used for the Chip Method, The test steps were:

1) Either a Q-Tip swab (Swab Method) was used to swab a one inch by one inch area of the epoxy material (test panel) and the swab was placed in test tube containing 1 millilter of water (Sample Tube) or, one or more fragments (Chip Method) from the epoxy material (test panel) was taken and placed in a test tube containing 1 milliliter of water (Sample Tube). The tube contents are a "Test Sample".
2) Three drops (0.12 milliliters, total) of EE ACh-E solution (0.25 units/ml in Reconstitution Buffer) was added to each Sample Tube containing the swab or fragments.
3) Each Sample Tube was capped and shaken to mix the contents.
4) Each Sample Tube was allowed to stand for 30 minutes at room temperature (65-68° F.).
5) Three drops (0.12 milliliters, total) of a solution of ATC Chloride (ATC-C) at a concentration of 3.95 mg/ml in distilled water were added to each Sample Tube.
6) Each Sample Tube was capped and shaken to mix contents;
7) Two drops (0.08 milliliters, total) of DTNB were added to each Sample Tube;
8) Each Sample Tube was capped and shaken to mix the contents;
9) Each Sample Tube was allowed to stand for 30 minutes at room temperature.
10) The intensity of each test sample was measured at 450 nm spectrophotometrically. Each test sample was also compared visually to a negative control—an epoxy sample known to not exhibit blush—and assessed as indicating the presence ("pos") or absence ("neg") of carbamates. The results are shown in Table 2 below. They show that the test worked well using Electric Eel ACh-E and ATC-C.

TABLE 2

| Method | | Absorbance 450 Negative Control | Absorbance 450 Test Sample | Inhibition (%) | Interpretation |
|---|---|---|---|---|---|
| Electric Eel ACh-E | Swab | 1.611 | 0.453 | 71.81 | pos |
| ATC-C | Swab | 2.395 | 0.353 | 85.29 | pos |
| Electric Eel ACh-E | Chip | 1.361 | 0.133 | 90.24 | pos |
| ATC-C | Chip | 2.375 | 0.308 | 87.02 | pos |

Example 3

The effect of pH on the test was investigated using the Swab test procedure described in for Example 1, except that the pH of the Assay Buffer (PBS) was adjusted. It was either adjusted to a low pH by using 2N HCL, and or to a high pH by using 2N NAOH. The results are summarized below in Table 3.

The panels for the Test samples in these Swab tests were the same as that used for the test panels in the Chip test in Example 2.

TABLE 3

| | Absorbance 450 Negative Control | Absorbance 450 Test Sample | Inhibition (%) |
|---|---|---|---|
| pH 3-4 (Nano Water) | 1.663 | 0.088 | 94.69 |
| pH 4.8 (1X PBS) | 0.337 | 0.04 | 88.28 |
| pH 7 (Nano Water) | 2.303 | 0.146 | 93.7 |
| pH 7.2 (1X PBS) | 1.984 | 0.169 | 91.5 |
| pH 9.5-10 (Nano Water) | 3.04 | 0.251 | 91.76 |
| pH 10.25 (1X PBS) | 2.058 | 0.283 | 86.3 |

"Nano water" refers to "nanopure water"; i.e., deionized water.

At all pH's tested the Test Sample swab could be shown to contain material that resulted in good inhibition of the ACh-E. Even though color development was dramatically reduced with 1X PBS-PH 4.8 good inhibition of the ACh-E was apparent. The reduced color development indicated that ACh-E has a lower activity at low pH.

What is claimes is:

1. A method for detecting the presence of amine blush in an amine-cured epoxy material, said method comprising the steps of:
   a. Collecting, in an aqueous solution, carbamates from said material, said aqueous solution being a test sample, said aqueous solution being a solution comprising water;
   b. Adding an enzyme whose activity is inhibited by carbamates to the test sample;
   c. Adding a substrate for said enzyme to the test sample such that cleavage of the substrate by the enzyme will result in either a modified substrate or a substrate cleavage product;
   d. Adding a chromogen to the test sample, such that said chromogen reacts with either the modified substrate or the substrate cleavage product so as to alter or intensify the color of the test sample;
   e. Subsequent to the foregoing steps (a), (b), (c), and (d) determining the intensity of the color of the test sample;
   f. Wherein the smaller the intensity of the color in the test sample, the greater the probability that the test sample suffers from amine blush.

2. The method of claim 1 wherein the enzyme is a cholinesterase, the substrate added is such that the cleavage of the substrate results in a cleavage product that comprises a thiol group, and the chromogen reacts with the cleavage product to alter the color of the test sample.

3. The method of claim 1 wherein the enzyme is an acetylcholinesterase, the substrate is acetylthiocholine or a salt thereof, and the chromogen is 5,5'-dithiobis-2-nitrobenzoic acid (DTNB).

4. The method of claim 1 wherein the collecting in step (a) comprises swabbing the amine cured epoxy material with a swab and then placing the swab in an aqueous solution so that carbamates within the swab will migrate from the swab into the aqueous solution so as to create the test sample.

5. The method of claim 1 wherein the collecting in step (a) comprises placing one or more fragments of the amine cured epoxy material into an aqueous solution so as to create the test sample.

6. The method of claim 1 wherein the intensity of the color is determined either by visual inspection of the test solution or spectrophotometically.

7. The method of claim 1 wherein a control is subjected to steps (b) through (f) in the same manner as the test sample is as subjected to those steps, said control selected from the group comprising a positive control and a negative control.

8. A kit comprising an enzyme that is inhibited by carbamates, a substrate for the enzyme, and a chromogen that reacts with either (i) the substrate as altered by the enzyme or (ii) with a substrate fragment resulting from substrate cleavage by the enzyme so that in either case (i) or (ii) the color of the chromogen in aqueous solution is altered.

9. The kit of claim 8 wherein the enzyme is a cholinesterase, the substrate is such that the cleavage of the substrate results in a cleavage product that comprises a thiol group, and the chromogen is one that reacts with the cleavage product in solution so as to change the color of the solution.

10. The kit of claim 8 comprising acetylthiocholine (ATC), 5,5'-dithiobis-2-nitrobenzoic acid (DTNB), and acetyl-cholinesterase (ACh-E).

11. The kit of claim 8 wherein said kit comprises a measuring device for determining whether the size of the epoxy material to be tested for the presence of carbamates conforms to an upper limit of volume or area, the measuring device preferably providing a two-dimensional area for assessing the size or amount of the epoxy material to be tested.

12. The kit of claim 8 wherein said kit further comprises a label or other printed material identifying a purpose of the kit as being the confirmation or demonstration of the presence of amine blush in an amine cured epoxy material.

13. The kit of claim 8 further comprising a swabbing device.

14. The method of claim 1 wherein the aqueous solution further comprises an alcohol.

15. The method of claim 2 wherein the aqueous solution further comprises an alcohol.

16. The method of claim 14 wherein the alcohol is selected from the group consisting of methanol and isopropyl alcohol.

17. The method of claim 15 wherein the alcohol is selected from the group consisting of methanol and isopropyl alcohol.

18. The method of claim 1 wherein the aqueous solution is 70% isopropyl alcohol.

19. The method of claim 2 wherein the aqueous solution is 70% isopropyl alcohol.

20. The method of claim 14 wherein the less the intensity of the color in the test sample, the greater the probability that in the test sample suffers from amine blush.

21. The method of claim 15 wherein the less the intensity of the color in the test sample, the greater the probability that in the test sample suffers from amine blush.

22. The method of claim 14 wherein a control is subjected to steps (b) through (f) in the same manner as the test sample is as subjected to those steps, said control selected from the group comprising a positive control and a negative control.

23. The method of claim 15 wherein a control is subjected to steps (b) through (f) in the same manner as the test sample is as subjected to those steps, said control selected from the group comprising a positive control and a negative control.

\* \* \* \* \*